United States Patent [19]
Wongsuragrai et al.

[11] Patent Number: 5,888,548
[45] Date of Patent: Mar. 30, 1999

[54] SPHERICALLY AGGLOMERATED STARCHES WITH SILICON DIOXIDE

[75] Inventors: Varatus Wongsuragrai; Aupakit Wongsuragrai; Saiyavit Varavinit, all of Bangkok, Thailand

[73] Assignee: Erawan Pharmaceutical Research and Laboratory Company Limited, Bangkok, Thailand

[21] Appl. No.: 704,854

[22] Filed: Aug. 27, 1996

[51] Int. Cl.$^6$ ........................................................ A61K 9/16
[52] U.S. Cl. ............................................ 424/489; 514/951
[58] Field of Search ..................... 424/489, 499; 514/951, 778

[56] References Cited

U.S. PATENT DOCUMENTS

| | | | |
|---|---|---|---|
| 3,725,556 | 4/1973 | Hanssen et al. | 514/770 |
| 4,016,337 | 4/1977 | Hsu | 426/99 |
| 4,021,582 | 5/1977 | Hsu | 426/99 |
| 4,072,535 | 2/1978 | Short et al. | 106/206.1 |
| 4,254,099 | 3/1981 | Asmussen et al. | 424/465 |
| 4,369,308 | 1/1983 | Trubiano | 536/106 |
| 4,601,895 | 7/1986 | Streuff et al. | 424/479 |
| 5,047,246 | 9/1991 | Gallian et al. | 424/464 |
| 5,585,115 | 12/1996 | Sherwood et al. | 424/489 |

OTHER PUBLICATIONS

Mitrevej et al. Production of Modified Rice Starch and its Utilization in the Pharmaceutical Industry. Micro. Util. Renewable Resource. 1989, vol. 6, pp. 153–157. Full Document.

Varavinit et al. Production of Spray Dried Rice Starch and its Utilization in the Pharmaceutical Industry. Microb. Util. Renewable Resource. 1989, vol. 6, pp. 158–162. Full Document.

Chemical Abstract Assession No. 113:218073, 1989.
Chemical Abstract Assession No. 113:218074, 1989.

*Primary Examiner*—Robert H. Harrison
*Attorney, Agent, or Firm*—Townsend and Townsend and Crew LLP

[57] ABSTRACT

Granules of starch or low protein rice flour are agglomerated to a larger size and a spherical shape by combining the granules with silicon dioxide and water to form a slurry, and drying the slurry by a spray dryer. The agglomerates have better flowability than the granules, and are readily used as direct compression fillers for tablets and capsules in drug or nutrient formulations. Tablets formed from these agglomerates have good hardness and friability, as well as favorable disintegration and dissolution characteristics. Chemically or physically modified starches can also be used, and starches other than rice starches can be included as well.

14 Claims, No Drawings

SPHERICALLY AGGLOMERATED STARCHES WITH SILICON DIOXIDE

This invention addresses the chemistry and physics of the evaporation of water from starch, and of the binding of starch granules and silicon dioxide into agglomerates.

BACKGROUND AND SUMMARY OF THE INVENTION

Processed starches in general do not have good flowability, and this limits their usefulness as fillers or carriers in drug formulations such as tablets and capsules.

The present invention resides in the formation of rice starches into spherical agglomerates by mixing the starches with silicon dioxide. The larger size and spherical shape of these agglomerates provide them with improved flowability that enables them to be used as a direct compression filler in tablet and capsule formulations. Tablets formed from these agglomerates exhibit good hardness, low friability, and favorable disintegration and dissolution characteristics. The agglomerates can also improve the flowability of powder-like substances which by themselves have poor flowability, by mixing the agglomerates with the powder so that the agglomerates serve as a carrier for the powder.

DETAILED DESCRIPTION OF THE INVENTION

In accordance with this invention, small granules of rice starch are mixed with silicon dioxide and water to form a slurry. Once formed, the slurry is stirred thoroughly, then dried by conventional means, a notable example being spray drying by the use of a centrifugal spray head at elevated temperature. Centrifugal spray heads are conventional equipment well known in the art of spray equipment.

The rice starch used to form the slurry can be unmodified rice starch as well as rice starch that has been chemically modified, physically modified, or both. Examples of chemically modified starches are starches that have been crosslinked, acetylated, oxidized, and otherwise treated, to achieve well-known starch derivatives. An example of a physical modification is pregelatinization of the starch by drum drying, followed by milling of the pregelatinized starch into a powder having a particle size capable of passing a 60–100 mesh sieve. These modified starches function as binders that further improve the agglomeration of the rice starch granules and silicon dioxide.

Rice flour generally has a protein content of about 6.5% to 7% by weight. For best results in the formation of agglomerates in accordance with this invention, however, rice flour having a protein content in the range of 0.2% to 5.0% is preferred. A protein content in this range can be achieved by soaking the rice in a dilute sodium hydroxide solution, then milling the rice with dilute sodium hydroxide, and washing off the rice protein from the slurry, for example by centrifugal separation. The resulting low-protein rice flour can then be dried by conventional methods such as flash drying, and in preferred embodiments of the invention, the dried particles can be screened by use of a 100-mesh sieve. Rice flour treated by these methods will have a lower protein content and a whiter appearance when compared to untreated flour.

The flowability of other starches which by themselves have poor flowability can be improved by mixing the agglomerates with the powder so that the agglomerates serve as a carrier for the powder. Examples of these other starches are tapioca starch, potato starch, corn starch, maize starch, sago starch, bean starch, and wheat starch, as well as other starches, and mixtures of two or more of these starches. These starches can also be chemically and/or physically modified in the same manner as that described above for the rice starch. Preferably, these additional starches will not exceed 25% by weight of the total composition, and most preferably will fall within the range of 1–25% by weight when present. The rice flour and/or rice starch used to form the slurry has an amylose content in the range of 0% to 40%.

The relative amounts of rice starch, silicon dioxide and water can vary considerably within the scope of this invention. Preferred amounts are 40% to 95% of a member selected from the group consisting of rice starch, low-protein rice flour, or a combination thereof, 0.1% to 50% silicon dioxide, and 1% to 15% water. Further preferred formulations are as follows, all percents by weight:

| | | |
|---|---|---|
| 1. | 40–95% | rice starch or low-protein rice flour |
| | 0.1–50% | silicon dioxide |
| | 5–15% | water |
| 2. | 30–85% | rice starch or low-protein rice flour |
| | 1–25% | chemically and/or physically modified rice starch |
| | 0.1–50% | silicon dioxide |
| | 5–15% | water |
| 3. | 30–85% | rice starch or low-protein rice flour |
| | 1–25% | chemically and/or physically modified rice starch |
| | 0.1–50% | silicon dioxide |
| | 5–15% | water |
| 4. | 30–85% | rice starch or low-protein rice flour |
| | 0–25% | tapioca starch |
| | 1–25% | chemically and/or physically modified tapioca starch |
| | 0.1–50% | silicon dioxide |
| | 5–15% | water |
| 5. | 30–85% | rice starch or low-protein rice flour |
| | 0–25% | tapioca starch |
| | 1–25% | chemically and/or physically modified rice starch |
| | 0.1–50% | silicon dioxide |
| | 5–15% | water |
| 6. | 30–85% | rice starch or low-protein rice flour |
| | 0–25% | tapioca starch |
| | 1–25% | chemically and/or physically modified tapioca starch |
| | 0.1–50% | silicon dioxide |
| | 5–15% | water |

The particle sizes of the spherical agglomerates are greater than the particles sizes of the starch granules used as a starting material, but the agglomerate size is not critical and can vary. In preferred embodiments of the invention, the agglomerate particle size is in the range of 20 to 1,000 microns in diameter, more preferably 50 to 200 microns in diameter, although agglomerates having a diameter of 100 microns or greater can be obtained by using a slurry of rice starch, silicon dioxide and water in which the rice starch constitutes 5–50% of the slurry (on a dry weight basis).

The formation of the agglomerates into tablets, capsules or other formulations is achieved by conventional methods well known in the pharmaceutical industry.

The following examples are offered for purposes of illustration.

EXAMPLE 1

A slurry is prepared by combining the following ingredients (all percents by weight):

| | |
|---|---|
| Rice starch or low-protein rice flour | 50% |
| Silicon dioxide | 1% |
| Water | 49% |

Agglomerates are formed from this slurry by spray drying.

EXAMPLE 2

A slurry is prepared by combining the following ingredients (all percents by weight):

| | |
|---|---|
| Rice starch or low-protein rice flour | 45% |
| Chemically and/or physically modified rice starch | 5% |
| Silicon dioxide | 1% |
| Water | 49% |

The chemically modified starch is starched that has been crosslinked, acetylated, or oxidized. The physically modified starch is starch that has been cooked and dried by drum drying, then milled into a powder having a particle size of 60–100 mesh by appropriate sieves. Once the slurry is formed, it is converted to agglomerates by spray drying.

EXAMPLE 3

A slurry is prepared by combining the following ingredients (all percents by weight):

| | |
|---|---|
| Rice starch or low-protein rice flour | 35% |
| Silicon dioxide | 10% |
| Chemically and/or physically modified rice starch | 5% |
| Water | 50% |

The chemically and/or physically modified rice starch is prepared as described in Example 2, and the slurry is converted to agglomerates by spray drying.

EXAMPLE 4

A slurry is prepared by combining the following ingredients (all percents by weight):

| | |
|---|---|
| Rice starch or low-protein rice starch | 25% |
| Silicon dioxide | 20% |
| Chemically and/or physically modified rice starch | 5% |
| Water | 50% |

The chemically and/or physically modified rice starch is prepared as described in Example 2, and the slurry is converted to agglomerates by spray drying.

EXAMPLE 5

A slurry is prepared by combining the following ingredients (all percents by weight):

| | |
|---|---|
| Rice starch or low-protein rice flour | 25% |
| Silicon dioxide | 20% |
| Chemically and/or physically modified tapioca starch | 5% |
| Water | 50% |

The chemically and/or physically modified tapioca starch is prepared in the same manner as described in Example 2 for the correspondingly modified rice starch, and the slurry is converted to agglomerates by spray drying.

EXAMPLE 6

A slurry is prepared by combining the following ingredients (all percents by weight):

| | |
|---|---|
| Rice starch or low-protein rice flour | 44% |
| Silicon dioxide | 1% |
| Tapioca starch | 5% |
| Water | 50% |

The slurry is converted to agglomerates by spray drying.

EXAMPLE 7

A slurry is prepared by combining the following ingredients (all percents by weight):

| | |
|---|---|
| Rice starch or low-protein rice starch | 39% |
| Silicon dioxide | 1% |
| Tapioca starch | 5% |
| Chemically and/or physically modified tapioca starch | 5% |
| Water | 50% |

The chemically and/or physically modified tapioca starch is prepared in the same manner as described in Example 2 for the correspondingly modified rice starch, and the slurry is converted to agglomerates by spray drying.

We claim:

1. Agglomerates comprising 40% to 95% of a member selected from the group consisting of rice starch, 0.2–5.0%-protein rice flour, and a combination thereof, 0.1% to 50% silicon dioxide, and 1% to 15% water, and formed by spray drying or by drying a slurry.

2. Agglomerates in accordance with claim 1 consisting of 40% to 95% of a member selected from the group consisting of rice starch, 0.2–5.0%-protein rice flour, and a combination thereof, 1% to 25% of a member selected from the group consisting of chemically modified rice starch, physically modified rice starch, and a combination thereof, 0.1% to 50% silicon dioxide, and 1% to 15% water.

3. Agglomerates in accordance with claim 1 consisting of 40% to 95% of a member selected from the group consisting of rice starch, 0.2–5.0%-protein rice flour, and a combination thereof, 25% or less tapioca starch, 0.1% to 50% silicon dioxide, and 1% to 15% water.

4. Agglomerates in accordance with claim 1 consisting of 40% to 95% of a member selected from the group consisting of rice starch, 0.2–5.0%-protein rice flour, and a combination thereof, 25% or less tapioca starch, 1% to 25% of a member selected from the group consisting of chemically modified rice starch, physically modified rice starch, and a combination thereof, 0.1% to 50% silicon dioxide, and 1% to 15% water.

5. Agglomerates in accordance with claim 1 in which said agglomerates are substantially spherical and have diameters in the range of 20 to 1,000 microns.

6. Agglomerates in accordance with claim 1 having an amylose content in a range of 0% to 40%.

7. Agglomerates in accordance with claim 1 consisting of 40% to 95% of a member selected from the group consisting of rice starch, 0.2–5.0%-protein rice flour, and a combination thereof, 0.1% to 50% silicon dioxide, 1% to 15% water, and 25% or less of a member selected from the group consisting of tapioca starch, potato starch, corn starch, sago starch, bean starch, wheat starch, and combinations thereof.

8. Agglomerates in accordance with claim 1 consisting of 40% to 95% of a member selected from the group consisting of rice starch, 0.2–5.0%-protein rice flour, and a combination thereof, 0.1% to 50% silicon dioxide, 1% to 15% water, and 25% or less of a member selected from the group consisting of tapioca starch, potato starch, corn starch, sago starch, bean starch, wheat starch, other starches, and combinations thereof, and 25% or less of chemically modified, physically modified, and combinations thereof of a member selected from the group consisting of tapioca starch, potato starch, corn starch, sago starch, bean starch, wheat starch, rice starch, and combinations thereof.

9. Agglomerates comprising 40% to 95% of a member selected from the group consisting of tapioca starch, potato starch, corn starch, sago starch, bean starch, wheat starch, and a combination thereof, 0 to 25% of a member selected from the group consisting of chemically modified, physically modified, and a combination thereof of tapioca starch, potato starch, corn starch, sago starch, bean starch, wheat starch, rice starch, other starch, other starches and a combination thereof; 0.1% to 50% silicon dioxide; and 1% to 15% waters and formed by spray drying or by drying a slurry.

10. Agglomerates comprising 40% to 95% of 0.2–5.0%-protein rice flour that has been pregelatinized and milled into a powder; 0.15 to 50% silicon dioxide, and 1% to 15% water.

11. Agglomerates in accordance with claim 10 further comprising tapioca starch that has been pregelatinized and milled into a powder in an amount no greater than 25% of said agglomerates.

12. Agglomerates in accordance with claim 10 further comprising tapioca starch that has been pregelatinized and milled into a powder in an amount no greater than 25% of said agglomerates, and a member selected from the group consisting of rice starch that has been pregelatinized and milled into a powder, rice starch that has been crosslinked, rice starch that has been acetylized, and rice starch that has been oxidized, in an amount no greater than 25% of said agglomerates.

13. Agglomerates in accordance with claim 10 further comprising a member selected from the group consisting of potato starch, corn starch, sago starch, bean starch, and wheat starch, that has been pregelatinized and milled into a powder, in an amount no greater than 25% of said agglomerates.

14. Agglomerates comprising 40% to 95% of 0.2–5.0%-protein rice flour selected from the group consisting of rice flour that has been pregelatinized and milled into a powder, rice flour that has been crosslinked, rice flour that has been acetylized, and rice flour that has been oxidized; 0.15 to 50% silicon dioxide, and 1% to 15% water.

* * * * *